(12) United States Patent
Robertson et al.

(10) Patent No.: US 10,426,688 B2
(45) Date of Patent: Oct. 1, 2019

(54) SYSTEMS AND METHODS FOR TRANSFERRING EXOSKELETON TRAJECTORY SEQUENCES

(71) Applicant: Ekso Bionics, Inc., Richmond, CA (US)

(72) Inventors: Brice Robertson, Oakland, CA (US); Matthew D. Sweeney, Sacramento, CA (US)

(73) Assignee: Ekso Bionics, Inc., Richmond, CA (US)

( * ) Notice: Subject to any disclaimer, the term of this patent is extended or adjusted under 35 U.S.C. 154(b) by 203 days.

(21) Appl. No.: 15/324,609

(22) PCT Filed: Jul. 7, 2015

(86) PCT No.: PCT/US2015/039352
§ 371 (c)(1),
(2) Date: Jan. 6, 2017

(87) PCT Pub. No.: WO2016/007493
PCT Pub. Date: Jan. 14, 2016

(65) Prior Publication Data
US 2017/0202725 A1    Jul. 20, 2017

Related U.S. Application Data

(60) Provisional application No. 62/021,906, filed on Jul. 8, 2014.

(51) Int. Cl.
*A61H 3/00* (2006.01)
*A61H 1/02* (2006.01)
(Continued)

(52) U.S. Cl.
CPC .............. *A61H 3/00* (2013.01); *A61H 1/024* (2013.01); *A61H 1/0244* (2013.01); *G06F 19/00* (2013.01);
(Continued)

(58) Field of Classification Search
CPC ........ A61H 1/024; A61H 1/0244; A61H 3/00; A61H 2201/165; A61H 2201/50;
(Continued)

(56) References Cited

U.S. PATENT DOCUMENTS

| 4,491,725 A | 1/1985 | Pritchard |
| 6,363,282 B1 | 3/2002 | Nichols et al. |

(Continued)

*Primary Examiner* — Rachid Bendidi
(74) *Attorney, Agent, or Firm* — Diederiks & Whitelaw, PLC.

(57) ABSTRACT

An exoskeleton trajectory sequence is received with at least one server, and the sequence is transferred to a first device where the sequence is validated. The validation includes a safety check in which a determination is made as to whether the sequence is safe for use with an exoskeleton. The validated sequence, or a confirmation that the sequence is valid, is received from the first device, and the validated sequence is offered for sale, license or lease. In one embodiment, a request for the sequence to be transferred is received from a first exoskeleton user. The sequence is validated and transferred to a second exoskeleton user. In another embodiment, a request for the sequence to be edited is received from an exoskeleton user. The sequence is edited, validated and transferred to the exoskeleton user.

15 Claims, 12 Drawing Sheets

(51) Int. Cl.
*G06Q 20/42* (2012.01)
*G06F 19/00* (2018.01)
*G16H 40/60* (2018.01)
*A61H 3/02* (2006.01)

(52) U.S. Cl.
CPC ............ *G06Q 20/42* (2013.01); *G16H 40/60* (2018.01); *A61H 3/02* (2013.01); *A61H 2003/0227* (2013.01); *A61H 2201/165* (2013.01); *A61H 2201/50* (2013.01); *A61H 2201/5012* (2013.01); *A61H 2201/5058* (2013.01); *A61H 2201/5071* (2013.01); *A61H 2201/5084* (2013.01); *A61H 2201/5097* (2013.01); *G05B 2219/40305* (2013.01)

(58) Field of Classification Search
CPC .... A61H 2201/5012; A61H 2201/5058; A61H 2201/5071; A61H 2201/5084; A61H 2201/5097; A61H 2003/0227; A61H 3/02; B25J 19/02; B25J 9/0006; G06F 19/00; G06Q 20/42; G16H 40/60; G05B 2219/40305
See application file for complete search history.

(56) References Cited

U.S. PATENT DOCUMENTS

| | | | |
|---|---|---|---|
| 7,149,773 | B2 | 12/2006 | Haller et al. |
| 7,711,603 | B2 | 5/2010 | Vanker et al. |
| 7,731,670 | B2 | 6/2010 | Aguirre-Ollinger et al. |
| 7,870,005 | B2 | 1/2011 | Arbogast et al. |
| 8,588,912 | B2 | 11/2013 | Hoyme et al. |
| 8,639,346 | B2 | 1/2014 | Seeberger et al. |
| 8,775,133 | B2 | 7/2014 | Schroeder |
| 8,996,173 | B2 | 3/2015 | Itkowitz et al. |
| 2005/0107726 | A1 | 5/2005 | Oyen et al. |
| 2007/0123997 | A1 | 3/2007 | Herr et al. |
| 2010/0292556 | A1 | 11/2010 | Golden |
| 2012/0172770 | A1* | 7/2012 | Almesfer ............... B25J 9/0006 601/35 |
| 2013/0198625 | A1* | 8/2013 | Anderson ............... G06F 3/016 715/701 |
| 2013/0291060 | A1 | 10/2013 | Moore |
| 2014/0100491 | A1 | 4/2014 | Hu et al. |

* cited by examiner

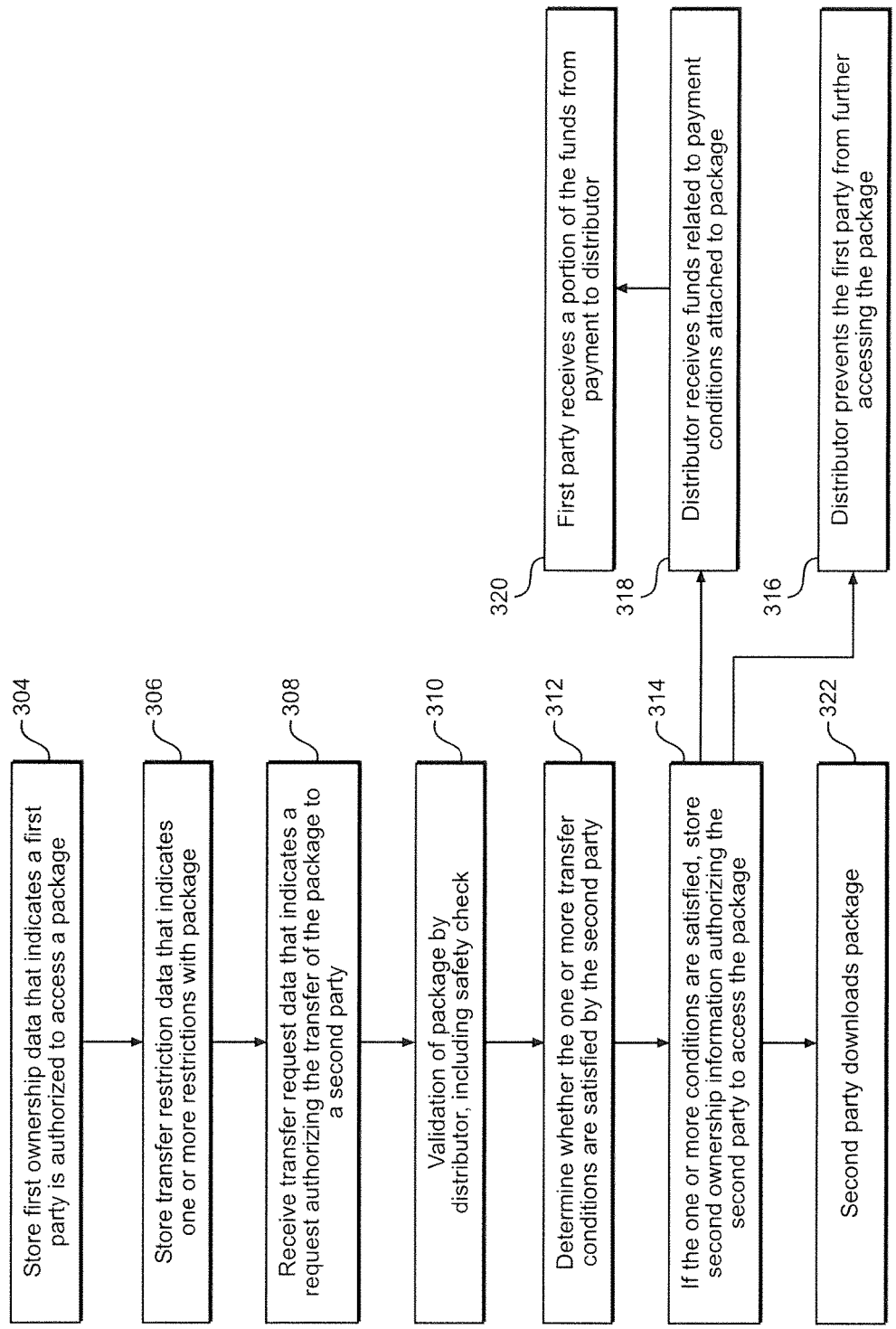

SYSTEMS AND METHODS FOR TRANSFERRING EXOSKELETON TRAJECTORY SEQUENCES

CROSS-REFERENCE TO RELATED APPLICATIONS

This application represents a National Stage application of PCT/US2015/039352, filed Jul. 7, 2015, which claims the benefit of U.S. Provisional Patent Application Ser. No. 62/021,906, which was filed on Jul. 8, 2014 and titled "Methods and Devices for the Communication and Validation of Instructions for Controlling the Motion of a Powered Orthotic Device". The entire content of these applications are incorporated by reference.

FIELD OF THE INVENTION

The present invention relates to a device and method that aids in the rehabilitation and restoration of muscular function in patients with impaired muscular function or control. More particularly, the present invention relates to a device and method suitable for therapeutic use with patients that have impaired neuromuscular/muscular function of the appendages, the device employing a motorized system of braces and related control systems that potentiate improved function of the appendages for activities including, but not limited to, walking.

BACKGROUND OF THE INVENTION

Millions of individuals suffer from either partial or total loss of walking ability, resulting in greatly impaired mobility for the affected individual. This disabled state can result from traumatic injury, stroke, or other medical conditions that cause disorders that affect muscular control. Regardless of origin, the onset and continuance of walking impairment can result in additional negative physical and/or psychological outcomes for the stricken individual. In order to improve the health and quality of life of patients with walking impairment, the development of devices and methods that can improve or restore walking function is of significant utility to the medical and therapeutic communities. Beyond walking impairment, there are a range of medical conditions that interfere with muscular control of the appendages, resulting in loss of function and other adverse conditions for the affected individual. The development of devices and methods to improve or restore these additional functions is also of great interest to the medical and therapeutic communities.

Human exoskeleton devices are being developed in the medical field to restore and rehabilitate proper muscle function for people with disorders that affect muscle control. These exoskeleton devices include a system of motorized braces that can apply forces to a wearer's appendages. In a rehabilitation setting, exoskeletons are controlled by a physical therapist who uses one of a plurality of possible input means to command an exoskeleton control system. In turn, the exoskeleton control system actuates the position of the motorized braces, resulting in the application of force to, and typically movement of, the body of the exoskeleton wearer. Exoskeleton control systems prescribe and control trajectories in the joints of the exoskeleton. These trajectories can be prescribed as position-based, force-based, or a combination of both methodologies, such as that seen in an impedance controller. Position-based control systems can modify exoskeleton trajectories directly through modification of the prescribed positions. Force-based control systems can modify exoskeleton trajectories through modification of the prescribed force profiles. Complicated exoskeleton movements, such as walking, are commanded by an exoskeleton control system through the use of a series of exoskeleton trajectories, with increasingly complicated exoskeleton movements requiring increasingly complicated series of exoskeleton trajectories. These series of trajectories may be cyclic, such as the exoskeleton taking a series of steps with each leg, or they may be discrete, such as an exoskeleton rising from a seated position into a standing position.

During a rehabilitation session and/or over the course of rehabilitation, it is highly beneficial for the physical therapist to have the ability to modify the prescribed positions and/or the prescribed force profiles depending on the particular physiology or rehabilitation stage of the patient. It is highly complex and difficult to construct an exoskeleton control interface that enables the full range of modification desired by a physical therapist during rehabilitation. In addition, it is important that the control interface not only allow the full range of modifications that may be desired by the physical therapist but also that the interface with the physical therapist be intuitive to the physical therapist, who may not be highly technically oriented. Even given an optimal control interface, certain physical therapists will be more skilled at creating exoskeleton trajectory sequences than others, and it is self-evident that an exoskeleton trajectory sequence produced by one physical therapist might be of use to a different physical therapist, even if only as a starting point for producing a modified trajectory sequence for a specific patient at a particular point in rehabilitation.

As exoskeleton design, control systems, and trajectory sequences improve, medical exoskeleton use will progress from use in rehabilitation settings to use by disabled individuals outside of rehabilitation. While the trajectory sequences used in rehabilitation are quite suitable for use in exoskeletons designed to increase the user's mobility (e.g., wheelchair replacement with an ambulatory exoskeleton), it should be recognized that if an exoskeleton can be made to allow a wearer to walk, then an exoskeleton can be made to allow a wearer to engage in more complicated activities such as dance or sports. However, the exoskeleton trajectories required for the highly complicated motions involved in such activities will be non-trivial to create and sequence, requiring the construction of these exoskeleton trajectory sequences by skilled physical therapists or other exoskeleton trajectory creators, likely with a substantial expenditure of time and labor. Once these complicated exoskeleton trajectory sequences have been created, it would be beneficial to other exoskeleton wearers or physical therapists to have access to the trajectory sequences. Similarly, advanced trajectory sequences may also soon be of use to able-bodied individuals for training and/or augmentation functions.

Methods have previously been developed that allow current exoskeletons to transmit exoskeleton trajectory information to a central server, such as EKSO PULSE™. However, a reverse system, in which trajectory information is transmitted from a central server to an exoskeleton control system, carries significant risks: an exoskeleton joint might be commanded to move outside of a safe range of motion; an exoskeleton might apply too much acceleration to an exoskeleton wearer; or unsafe trajectories may unbalance an exoskeleton, resulting in injury to the exoskeleton wearer. Moreover, it must further be considered that what is safe for one specific exoskeleton wearer may not be safe for another, depending on the wearer's mass and proportions, extent of disability/rehabilitative state, and skill level at exoskeleton operation—with these considerations in some cases requiring modification of trajectories for different users. Furthermore, the United States Food and Drug Administration (FDA) requires that medical devices be proven to be safe, and, as such, the safety of exoskeleton trajectory packages should be clearly and consistently demonstrated.

Accordingly, there exists an unmet need to develop a method and device that allows for exoskeleton trajectory sequence creators to be able to distribute, with satisfaction of certain terms including payment, exoskeleton trajectory sequences to other exoskeleton users. There also exists an unmet met need to provide a method and device that demonstrates, to the satisfaction of applicable regulatory authorities, that the exoskeleton trajectory sequences considered for distribution are safe. As such, the distribution system preferably also includes a validation component, including but not limited to a safety check of the exoskeleton trajectory sequence, prior to the transfer of a trajectory sequence to a new exoskeleton/exoskeleton user.

SUMMARY OF THE INVENTION

It is an object of the present invention to provide a device and method that allows a physical therapist or other exoskeleton trajectory creator to create exoskeleton trajectory sequences and upload those trajectory sequence packages to a central server (or cloud). This allows for the later distribution (e.g., by downloading) of the uploaded trajectory sequence packages to an exoskeleton trajectory user upon the satisfaction of one or more terms required by the exoskeleton creator and trajectory distributor, including but not limited to payment.

It is an additional object of the present invention to provide a device and method that allows for the validation of the uploaded trajectory sequence packages prior to distribution of these trajectory packages in order to confirm the safety or other attributes of these uploaded exoskeleton trajectory sequence packages. It is an object of this invention that this validation system is sufficient to satisfy governmental regulatory (e.g., FDA) requirements relating to the safety of trajectory sequence packages for use with exoskeletons.

It is an additional object of the present invention to provide a device and method that allows an exoskeleton trajectory sequence owner to sell, lease, license ownership of an exoskeleton trajectory sequence and transfer that exoskeleton trajectory sequence to secondary exoskeleton trajectory users once the exoskeleton trajectory package has been validated by the exoskeleton trajectory package distributor in order to confirm the safety or other attributes of these uploaded exoskeleton trajectory sequence packages for use by the secondary exoskeleton wearer.

It is an additional object of the present invention to provide a device and method that allows a physical therapist or other exoskeleton trajectory sequence editor/tuner to modify or tune an exoskeleton trajectory sequence owned by a separate exoskeleton user as a service upon validation of the modified exoskeleton trajectory sequence by the exoskeleton trajectory package distributor in regards to a specific exoskeleton wearer and upon satisfaction of one or more terms required by the exoskeleton trajectory sequence editor/tuner.

Concepts were developed for means by which a physical therapist, or other person skilled in the art of exoskeleton trajectory design, can upload exoskeleton trajectory sequence packages to a central exoskeleton trajectory distribution server, with ownership information, licensing terms, and descriptive information attached to these trajectory packages. The central trajectory distribution server operator then performs analyses on the uploaded trajectory packages for validation of safety or other features of the trajectory packages, at which point the trajectory packages and descriptive information are indexed and made available for download by other exoskeleton users or other parties who might be interested in acquiring a specific exoskeleton trajectory package. Upon selection of an indexed trajectory package for download, the party interested in acquiring the trajectory package then satisfies certain transfer payment terms, resulting in a license, lease, or purchase of the trajectory package, with some portion of this payment going to the exoskeleton trajectory sequence creator and another portion of this payment going to the entity operating the central exoskeleton trajectory distribution server and validation service.

Concepts were further developed to allow a primary party, who has some ownership right, such as by way of license, purchase, or lease, to an exoskeleton trajectory sequence package, to transfer that ownership right to a secondary party upon the validation of the trajectory package by the central exoskeleton trajectory distribution server operator and the fulfillment of payment terms by the secondary party. A portion of this payment goes to the primary party and another portion of this payment goes to the entity operating the central exoskeleton trajectory distribution server and validation service.

Concepts were additionally developed for allowing the owner of an exoskeleton trajectory package to hire a physical therapist, or other person skilled in the art of exoskeleton trajectory design, to modify or tune exoskeleton trajectories, with the modified trajectories then being validated by the central exoskeleton trajectory distribution server operator and with some portion of the payment for these services going to the physical therapist and another portion of the payment going to the entity operating the central exoskeleton trajectory distribution server and validation service.

In particular, the present invention is directed to systems and methods for transferring exoskeleton trajectory sequences. In one embodiment, a sequence is received with at least one server, and the sequence is transferred to a first device where the sequence is validated. The validation includes a safety check in which a determination is made as to whether the sequence is safe for use with an exoskeleton. The validated sequence, or a confirmation that the sequence is valid, is received from the first device with the at least one server. The validated sequence is offered for sale, license or lease, and, if the sequence is sold, licensed or leased, the sequence is transferred to a second device. Also, a payment is received if the sequence is sold, licensed or leased. At least a portion of the payment is transferred to a creator of the sequence. In one embodiment, the sequence is created using an exoskeleton.

Preferably, the first device includes an exoskeleton, and the safety check includes performing a physical test of the sequence using the exoskeleton. Performing the physical test includes causing the exoskeleton to move and receiving data from a sensor of the exoskeleton. The physical test is performed while the exoskeleton is worn by a person or an anthropomorphic device.

In another embodiment, a request for a sequence to be transferred is received from a first exoskeleton user with the at least one server. The sequence is transferred to a first device where the sequence is validated. The validated sequence, or a confirmation that the sequence is valid, is received from the first device with the at least one server. The validated sequence is transferred to a second exoskeleton user, and the first exoskeleton user is prevented from using or accessing the sequence. Also, a payment is received from the second exoskeleton user, and at least a portion of the payment is transferred to the first exoskeleton user.

Preferably, the validation includes determining whether the sequence is safe for use by the second exoskeleton user. Determining whether the sequence is safe for use by the second exoskeleton user includes taking into account physical attributes of the second exoskeleton user. In one embodiment, the first device includes an exoskeleton, and determining whether the sequence is safe for use by the second exoskeleton user includes performing a physical test of the sequence using the exoskeleton. In other embodiments, transferring the validated sequence to the second exoskeleton user includes transferring the validated sequence to an exoskeleton of the second user, and preventing the first exoskeleton user from using or accessing the sequence includes preventing an exoskeleton of the first exoskeleton user from performing the sequence.

In still another embodiment, a request for a sequence to be edited is received from an exoskeleton user with the at least one server. The sequence is transferred to a first device where the sequence is edited. The edited sequence is transferred to a second device where the sequence is validated. The validated sequence, or a confirmation that the sequence is valid, is received from the second device with the at least one server. The validated sequence is transferred to the exoskeleton user. Also, a payment is received from the exoskeleton user, and at least a portion of the payment is transferred to the editor.

Preferably, the validated includes determining whether the sequence is safe for use by the exoskeleton user. Determining whether the sequence is safe for use by the exoskeleton user includes taking into account physical attributes of the exoskeleton user. In one embodiment, the second device includes an exoskeleton, and determining whether the sequence is safe for use by the exoskeleton user includes performing a physical test of the sequence using the exoskeleton. In other embodiments, the first device includes an exoskeleton, and transferring the sequence to the first device includes transferring the sequence to the exoskeleton. Transferring the validated sequence to the second exoskeleton user includes transferring the validated sequence to an exoskeleton of the second exoskeleton user.

Additional objects, features and advantages of the invention will become more readily apparent from the following detailed description of preferred embodiments thereof when taken in conjunction with the drawings wherein like reference numerals refer to common parts in the several views.

BRIEF DESCRIPTION OF THE FIGURES

FIG. 3B is a flowchart in accordance with the second embodiment in which a licensed exoskeleton trajectory sequence is sold and transferred from one exoskeleton user to a second exoskeleton user via an intermediary, with this intermediary performing validation of the exoskeleton trajectory sequence for parameters including safety;

DETAILED DESCRIPTION OF THE INVENTION

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to employ the present invention.

Figure 1:
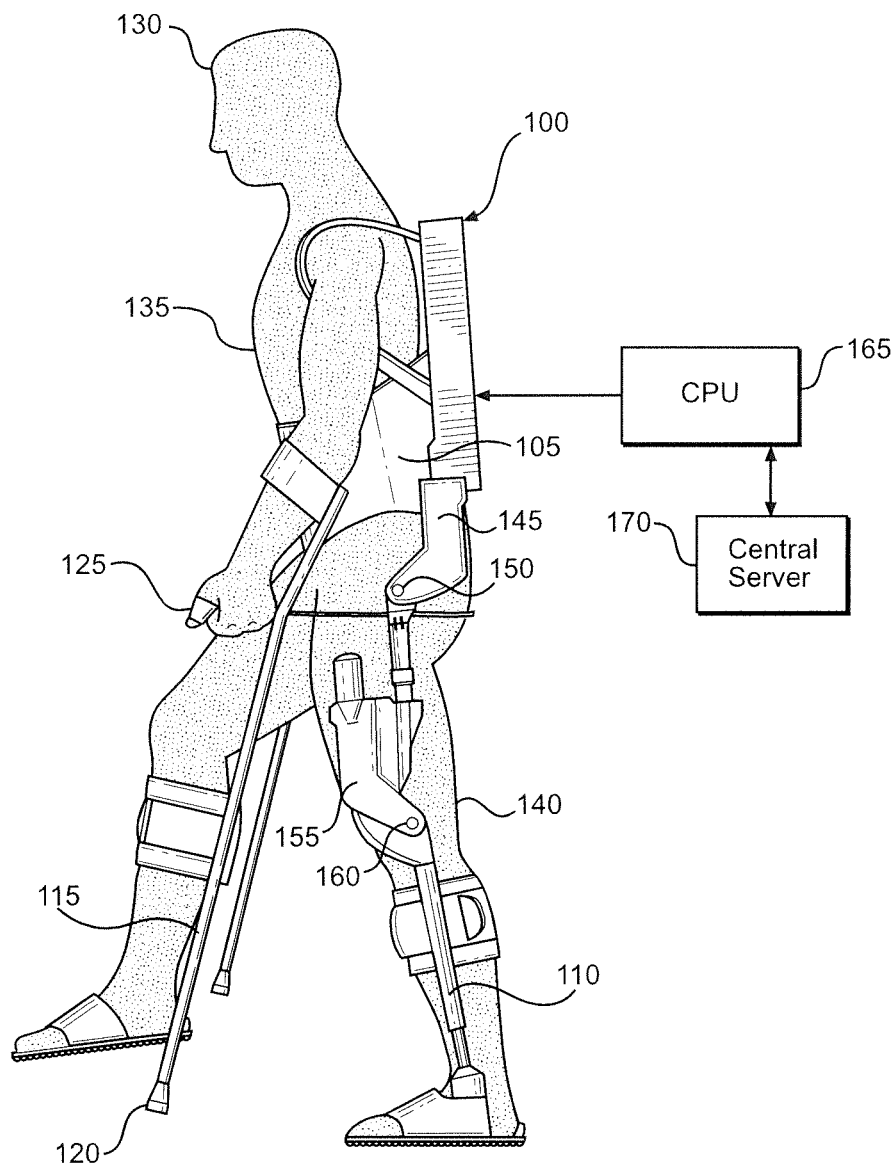
FIG. 1 is a side view of an individual coupled to an ambulatory exoskeleton, with a control system of the exoskeleton in communication with a central server in accordance with the present invention.

With reference to FIG. 1, an exoskeleton 100 has a torso portion 105 and leg supports (one of which is labeled 110). Exoskeleton 100 is used in combination with a pair of crutches, a left crutch 115 of which includes a lower, ground engaging tip 120 and a handle 125. In connection with this embodiment, through the use of exoskeleton 100, a patient (or, more generally, a wearer or user) 130 is able to walk. In a manner known in the art, torso portion 105 is configured to be coupled to a torso 135 of patient 130, while the leg supports are configured to be coupled to the lower limbs (one of which is labeled 140) of patient 130. Additionally, actuators, interposed between portions of the leg supports 110, as well as between the leg supports 110 and torso portion 105, are provided for shifting of the leg supports 110 relative to torso portion 105 to enable movement of the lower limbs 140 of patient 130. In some embodiments, torso portion 105 can be quite small and comprise a pelvic link (not shown), which wraps around the pelvis of patient 130.

In the example shown in FIG. 1, the actuators are specifically shown as a hip actuator 145, which is used to move a hip joint 150 in flexion and extension, and as knee actuator 155, which is used to move a knee joint 160 in flexion and extension. The actuators 145 and 155 are controlled by a controller (or CPU) 165 in a plurality of ways known to one skilled in the art of exoskeleton control, with controller 165 being a constituent of an exoskeleton control system. Although not shown in FIG. 1, various sensors are in communication with controller 165 so that controller 165 can monitor the orientation of exoskeleton 100. Such sensors can include, without restriction, encoders, potentiometers, accelerometer and gyroscopes, for example. In addition, controller 165 is in either continuous or intermittent communication with, and reports all collected data to, a central server 170. As certain particular structure of an exoskeleton for use in connection with the present invention can take various forms and is known in the art, it will not be detailed further herein.

Figure 2A:
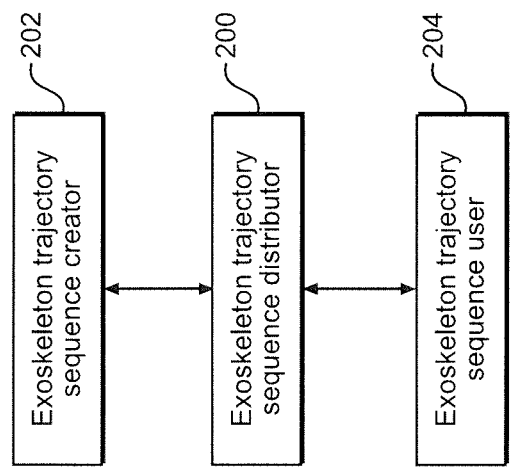
FIG. 2A is a block diagram showing the parties that are communicating in a first embodiment of the present invention.
Figure 2B:
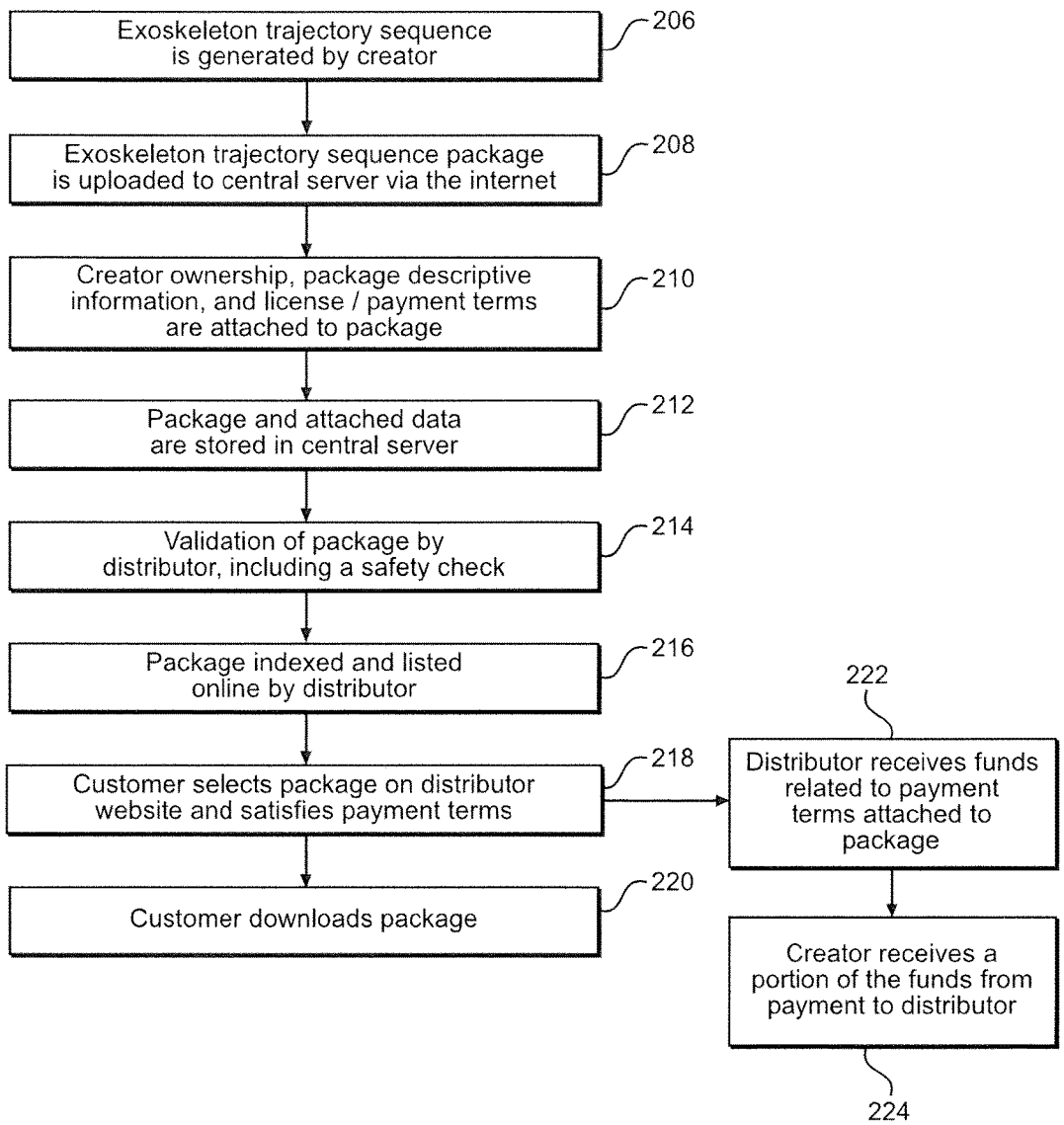
FIG. 2B is a flowchart in accordance the first embodiment in which an exoskeleton trajectory sequence is licensed and distributed from an exoskeleton trajectory sequence creator to an exoskeleton trajectory sequence user via an intermediary, with this intermediary performing validation of the exoskeleton trajectory sequence for parameters including safety.

With reference to FIG. 2A, an exoskeleton trajectory sequence distributor 200 is shown in communication with an exoskeleton trajectory sequence creator 202 and exoskeleton trajectory sequence user 204 in accordance with a first embodiment of the present invention. A flow diagram in accordance with the first embodiment is illustrated in FIG. 2B. With continued reference to FIG. 2B, at step 206, an exoskeleton trajectory sequence is generated by creator 202. At step 208, an exoskeleton trajectory sequence package (containing the exoskeleton trajectory sequence) is uploaded to central server 170 via the internet or by another communication means known to those skilled in the art. At step 210, creator ownership, package descriptive information, and license/payment terms are attached to the package. At step 212, the package and attached data are stored in central server 170. At step 214, the package is validated by distributor 200, the validation including a safety check. Upon a successful validation in step 214, the package is indexed and listed online by distributor 200 or presented in another digital or physical format in step 216. At step 218, a customer (i.e., user 204) selects a package on a website of distributor 200 (or another listing means such as a dedicated app) and satisfies the payment terms attached to the package. Upon satisfaction of the payment terms in step 218, the customer downloads the package in step 220. At step 222, distributor 200 receives funds in accordance with the payment terms attached to the package. At step 224, distributor 200 then transfers an agreed upon portion of the funds received in step 222 to creator 202. In some embodiments, storage in step 212 occurs in the cloud rather than on central server 170. In some embodiments, the safety check/validation performed in step 214 occurs solely in silico (i.e., it is performed on computer or via computer simulation). In other embodiments, the safety check/validation performed on the package in step 214 includes one or more physical tests. These physical tests can involve, but are not limited to, testing upon an exoskeleton being worn by an anthropomorphic test device, such as a crash test dummy, which can fitted with accelerometers, pressure sensors, and/or other sensors as discussed in further detail in connection with FIG. 2D.

Figure 2C:
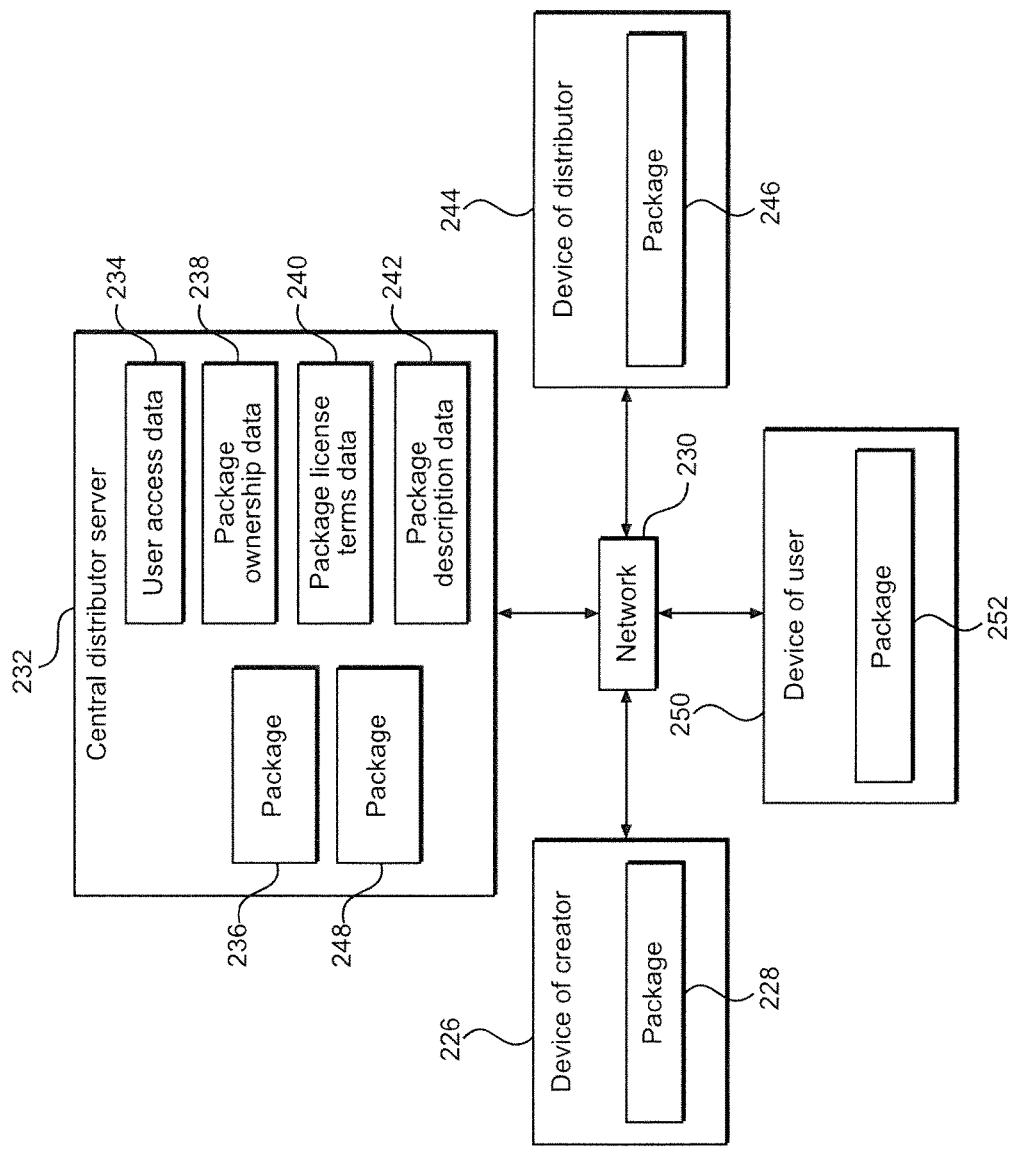
FIG. 2C is a block diagram showing the devices and digital content in communication in the first embodiment.

With reference to FIG. 2C, a block diagram shows the devices and digital content in communication in accordance with the first embodiment. A device 226 of creator 202 contains a stored digital content item: an exoskeleton trajectory sequence package 228. Device 226 is in communication with a network 230, which is also in communication with a central distribution server 232. Server 232 knows the identity of device 226 based on user access data 234. Device 226 uploads package 228 via network 230 to server 232, which saves a copy of the content of package 228 as an exoskeleton trajectory sequence package 236 to which package ownership data 238 is attached based on user access data 234 and device 226. Device 226 also uploads package license terms data 240 and a package description data 242 to server 232 via network 230. Upon completion of the saving of package 236 and associated package ownership data 238, package license terms data 240, and package description data 242, server 232 transfers package 236 via network 230 to a device 244 of distributor 200 where a copy of the content of package 236 is saved as an exoskeleton trajectory sequence package 246. Device 244 is used to validate package 246 as described above in connection with step 214. Upon successful validation of package 246, device 244 uploads package 246 via network 230 to server 232 where a copy is saved as an exoskeleton trajectory sequence package 248. User access data 234 is then modified to show package 248 as available for license, and associated package ownership data 238, package license terms data 240, and package description data 242 are now indicated as being available to exoskeleton trajectory sequence users (e.g., user 204) based on user access data 234. At this point, a device 250 of user 204, which is in communication with server 232 via network 230, is able view package 248 and its associated package ownership data 238, package license terms data 240, and package description data 242. Upon satisfaction of package license terms data 240 as described above in connection with step 218, server 232 updates user access data 234 and package ownership data 238 to allow download of package 248 via network 230 to device 250 of user 240 where a copy of the content contained in package 248 is stored as an exoskeleton trajectory sequence package 252.

Figure 2D:
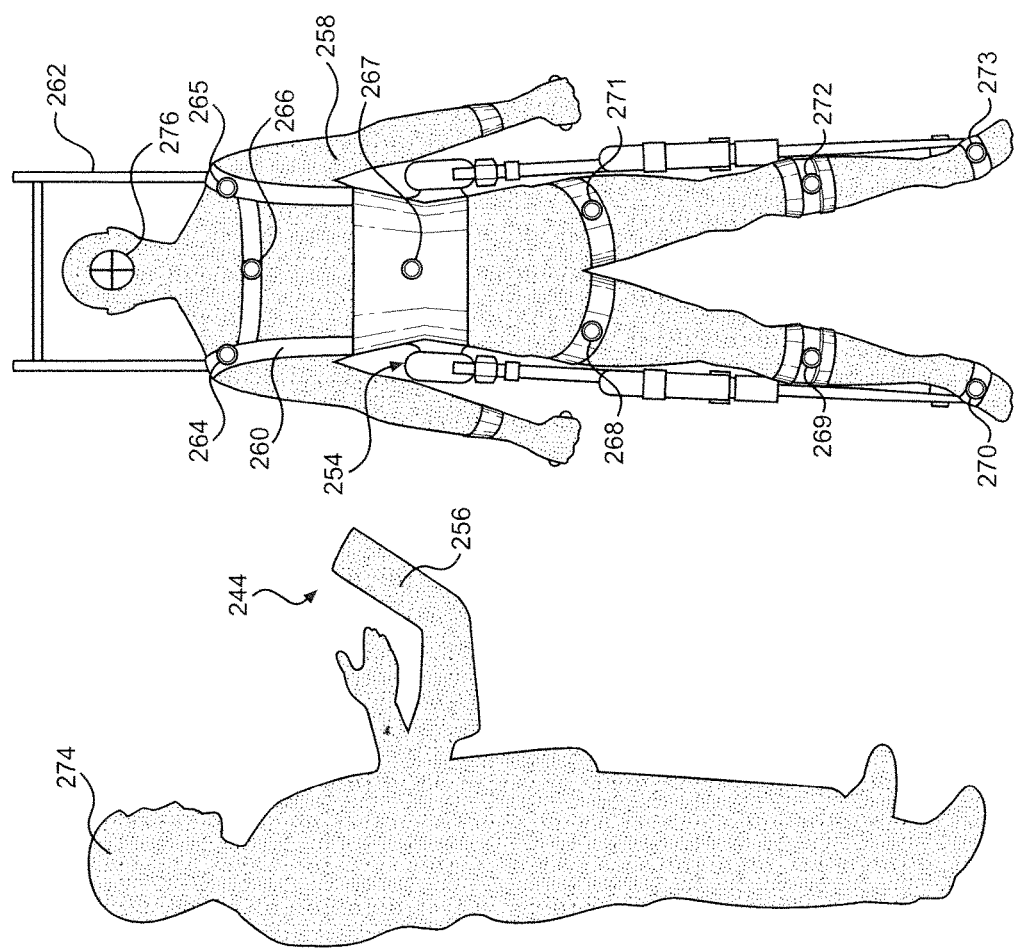
FIG. 2D shows a first example of an exoskeleton trajectory sequence safety validation device in accordance with the first embodiment.

With reference to FIG. 2D, device 244 of distributor 200 is shown being used to validate package 246 uploaded by creator 202 in accordance with the first embodiment. Specifically, device 244 comprises an exoskeleton 254 and a computer 256. An anthropomorphic test device 258, which is shown as a crash test dummy, is attached to exoskeleton 254 by strapping 260, and both test device 258 and exoskeleton 254 are suspended by an adjustable harness 262. Exoskeleton 254 is fitted with a plurality of sensors 264-273, which are in communication with computer 256. Preferably, sensors 264-273 are the sensors already provided for use in controlling the motion of exoskeleton 254. A validation engineer 274 interacts with computer 256, which not only collects data from sensors 264-273 but also controls exoskeleton 254 (and movement thereof). This allows engineer 274 to initiate testing of package 246. In some embodiments, test device 258 contains additional sensors (one of which is labeled 276) that are in communication with computer 256. Additionally, sensors 264-273 and 276 can be accelerometers, pressure sensors, motion capture systems, inertial measurement units, other types of sensors known to those skilled in the art or a combination of such sensors. It should also be recognized that sensors 264-273 and 276 can be placed in more or different locations than those shown in FIG. 2D or found on current exoskeletons. Also, in some embodiments, engineer 274 is not physically present during validation testing but instead receives data remotely or at a different time. In some embodiments, engineer 274 takes attributes of a specific exoskeleton user into account for safety purposes since what is safe for one user might not be safe for another user. The attributes accounted for can include but are not limited to mass, dimensions, age, flexibility, balance, injury type/extent, rehabilitative state, or even skill level of exoskeleton operation. In some embodiments, the function of engineer 274 is supplemented or replaced by a computer (more specifically, an algorithm implemented by a computer). In some embodiments, harness 260 is attached to one or more systems that allow it to move in the transverse, sagittal, or coronal planes so that the harness is able to balance and/or move with a moving exoskeleton.

Figure 2E:
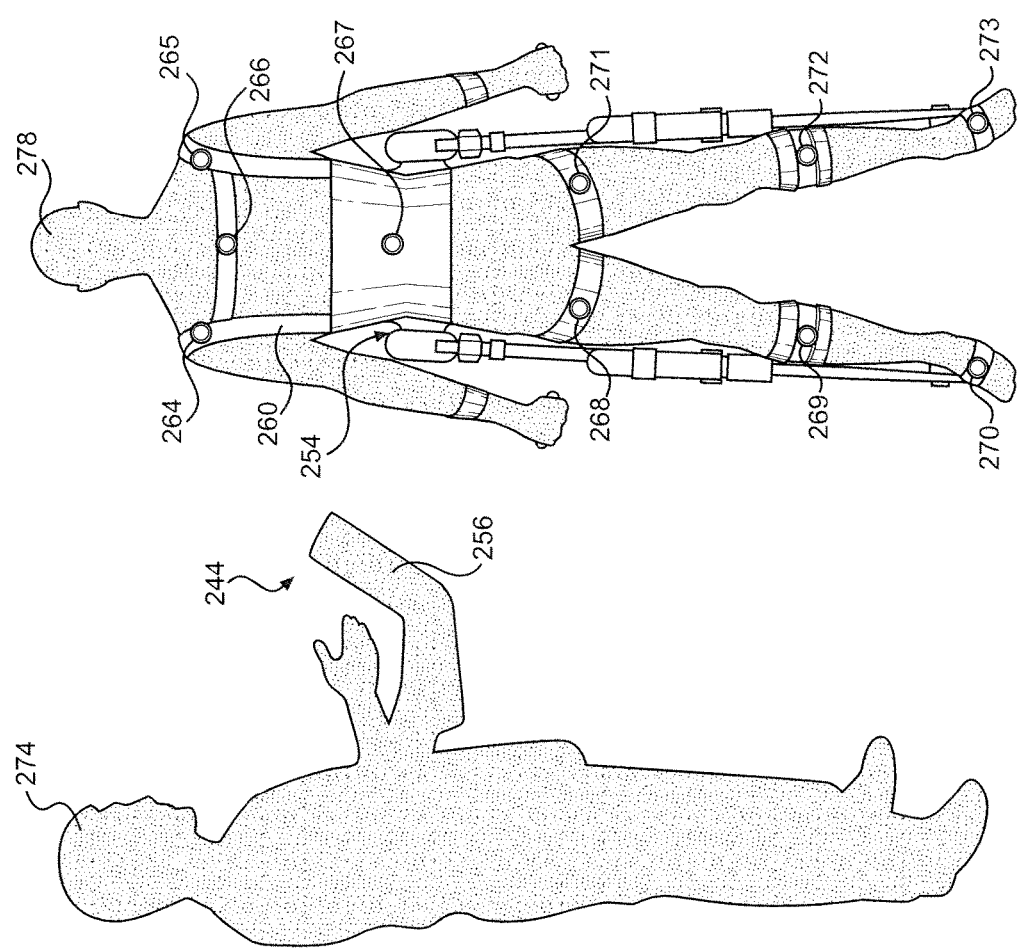
FIG. 2E shows a second example of an exoskeleton trajectory sequence safety validation device in accordance with the first embodiment.

With reference to FIG. 2E, device 244 is shown being used to validate package 246 in accordance with the first embodiment. As with the embodiment shown in FIG. 2D, device 244 comprises exoskeleton 254 and computer 256. However, in place of test device 258, an exoskeleton test pilot 278 is coupled to exoskeleton 254 by strapping 260. As described above, exoskeleton 254 is fitted with sensors 264-273 that are in communication with computer 256. Engineer 274 interacts with computer 256, which not only collects data from sensors 264-273 but also controls exoskeleton 254, allowing engineer 274 to initiate testing of package 246. Test pilot 278 is also in communication with engineer 274, and, upon initiation of exoskeleton package 246 by engineer 274, both engineer 274 and test pilot 278 collaborate in the evaluation of package 246. In some embodiments, test pilot 278 is able-bodied, and, in other embodiments, test pilot 278 is disabled. Also, in some embodiments, test pilot 278 is a physical therapist. Furthermore, in some embodiments, test pilot 278 also evaluates additional content that may be related to or contained in an exoskeleton trajectory sequence package, such as exoskeleton feedback to the wearer, exoskeleton balance/guidance information, or any other exoskeleton-wearer interface known in the art.

As an example of the first embodiment, consider a trajectory sequence creator who produces an exoskeleton trajectory sequence that allows an exoskeleton and wearer to walk laterally. This package and its attached data are uploaded to a distributor's server. Once uploaded, the package is validated by the distributor and shown to safely allow an exoskeleton and wearer to walk laterally. The package is then posted on the distributor's website where it is accessible to exoskeleton users. One of these users, a disabled individual who cannot walk without an exoskeleton, wishes to be able to walk laterally in his exoskeleton. The user purchases or licenses the package from the website and then downloads the package into his exoskeleton. The user is now able to walk laterally in his exoskeleton, the creator is compensated for his work in creating the package, and the distributor is compensated for facilitating the transaction. The overall result is an improvement in exoskeleton usability for exoskeleton users as more packages are developed by incentivized creators.

Figure 3A:
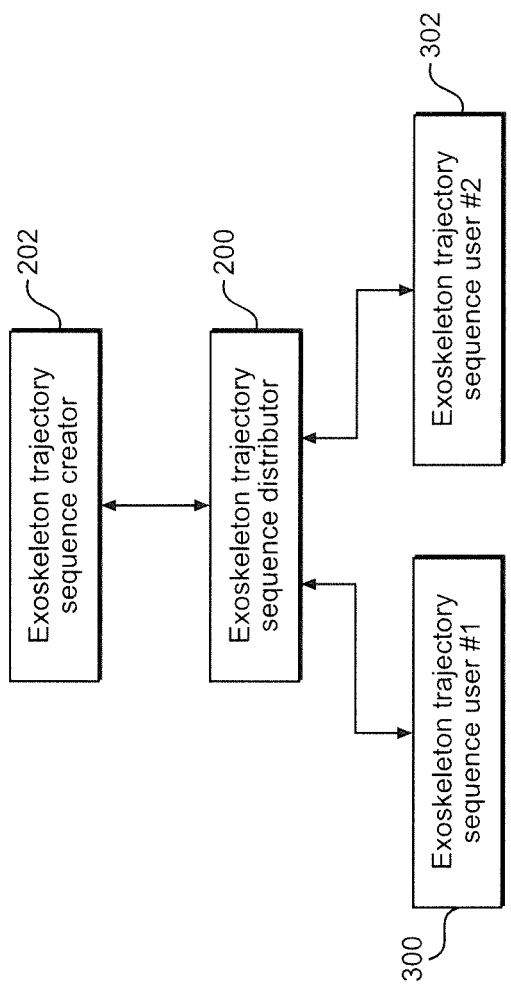
FIG. 3A is a block diagram showing the parties that are communicating in a second embodiment of the present invention.

With reference to FIG. 3A, a second embodiment of the present invention is illustrated in which distributor 200 is in communication with a first exoskeleton trajectory sequence user 300 and a second exoskeleton trajectory sequence user 302. A flow diagram of the second embodiment is provided in FIG. 3B. With continued reference to FIG. 3B, distributor 200 stores first ownership data at step 304. This first ownership data indicates that first user 300 is authorized to access a given exoskeleton trajectory sequence package, which can be acquired by first user 300 as discussed above. At step 306, distributor 200 stores transfer restriction data that indicates one or more restrictions with the package. At step 308, distributor 200 receives transfer request data that indicates a request authorizing the transfer of the package to second user 302. At step 310, distributor 200 performs a validation on the package in order to assure safety and other features of the package. Upon validation for the package in step 310, distributor 200 determines whether one or more transfer conditions are satisfied by second user 302 in step 312. At step 314, if the one or more conditions are satisfied, distributor 200 stores second ownership information authorizing second user 302 to access the package, and, in step 316, distributor 200 prevents first user 300 from further accessing the trajectories package. At step 318, distributor 200 receives funds related to payment conditions attached to the package. At step 320, the first user 300 receives a portion of the funds from the payment to distributor 200. At step 322, second user 302 downloads the package. In some embodiments, the validation of step 310 can be a simple file comparison with stored backup data of the original package validated by distributor 200. In other embodiments, step 310 is a full validation and safety check (as described in connection with the first embodiment). In some embodiments, the validation and safety checks of step 310 take into account the differences between the users of the exoskeleton devices, such as weight, flexibility, and balance since what is safe for one user may not be safe for another.

Figure 3C:
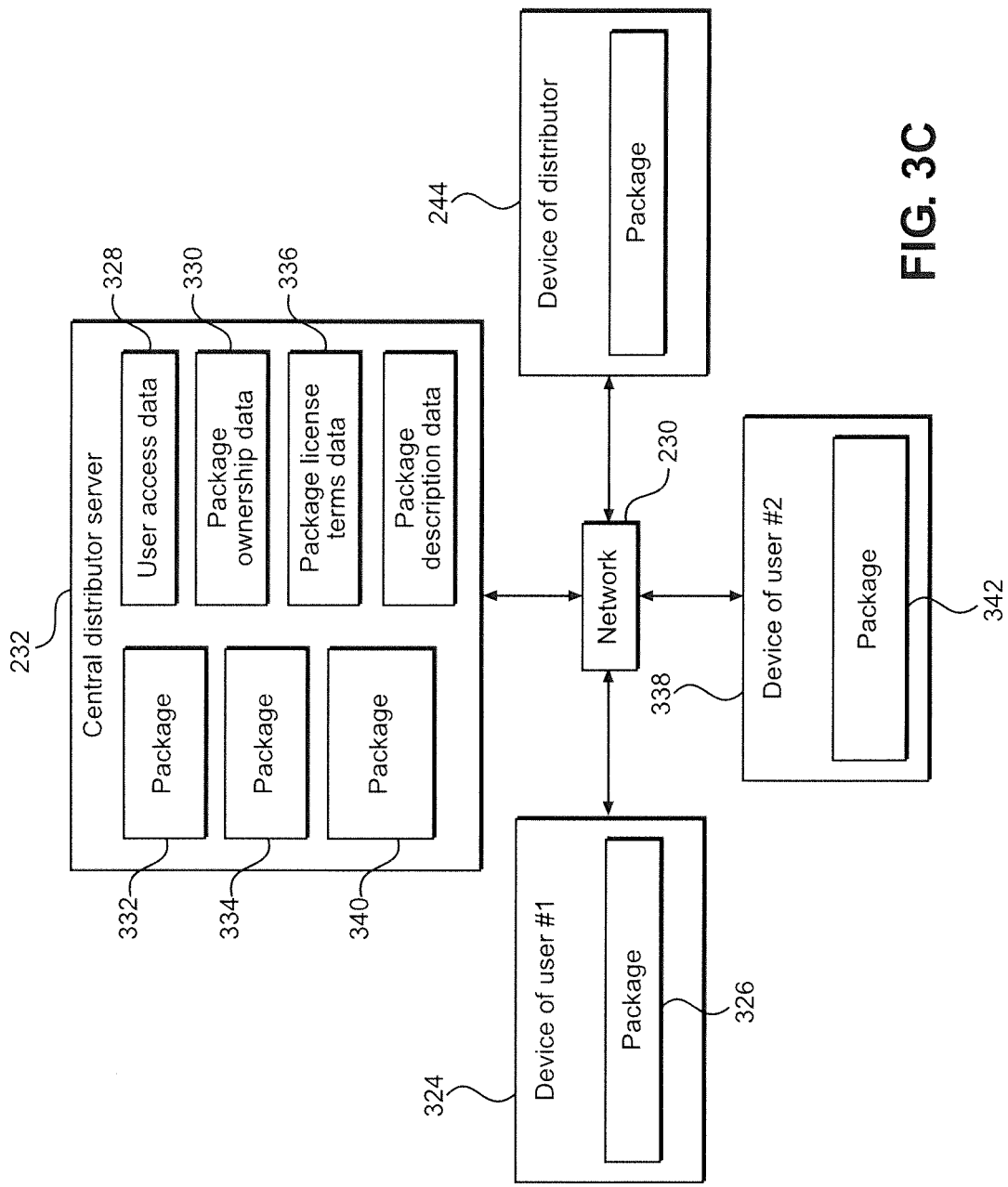
FIG. 3C is a block diagram showing the devices and digital content in communication in the second embodiment.

With reference to FIG. 3C, a block diagram shows the devices and digital content in communication in accordance with the second embodiment. A device 324 of first user 300 contains a stored digital content item: an exoskeleton trajectory sequence package 326. As with the first embodiment, device 324 is in communication with network 230, which is also in communication with server 232. Server 232 knows the identity of device 324 based on user access data 328. In addition, package ownership data 330 is stored within server 232. Based on user access data 328 and ownership data 330, server 232 confirms that device 324 is an authorized licensee, or other owner type, of package 326, which is a duplicate of an exoskeleton trajectory sequence package 332 that is stored on server 232. Device 324 indicates to server 232 via network 230 that it wishes to make package 326 available for resale or license transfer. Device 244 of distributor 200 had previously performed validation and a safety check on an exoskeleton trajectory sequence package 334, the parent file for an exoskeleton trajectory sequence package 332. Server 232 and device 244 confirm that both package 326 and package 334 are the same file. Upon this confirmation, server 232 alters user access data 328 to show that device 324 has a copy of package 326 for resale or relicense in accordance with package license terms data 336 stored on server 232. A device 338 of second user 302, which is in communication with server 232 through network 230, is now able to view the copy of package 326 for resale or relicense by device 324. Upon completion of the resale or relicense terms by second user 302 in accordance with package license terms data 336 stored on server 232, package 326 is deleted from device 324, and device 324 is prevented from further access to any copies of package 334 either by alteration of package ownership data 330 or by deletion of package 332, which was the file stored on server 232 from which device 324 originally had access. At the same time, server 232 creates a new copy of package 332: an exoskeleton trajectory sequence package 340, to which is attached new package ownership data indicating licensing of package 340 by device 338. Device 338 then downloads package 340 and stores this file as an exoskeleton trajectory sequence package 342. In some embodiments, device 324 of first user 300 is able to alter package license terms data 336 for the "used" package 326. In other embodiments, package license terms data 336 is controlled solely by creator 202 and/or distributor 200.

As an example of the second embodiment, consider a disabled exoskeleton wearer who has a daughter who was recently married. This wearer wanted to be able to dance with his daughter at her wedding and, prior to the wedding, purchased an exoskeleton trajectory sequence package that allowed the wearer to dance the waltz. After the wedding had passed, the wearer had no further use for waltzing and wished to resell the package. Through an implementation of the second embodiment of the present invention, a distributor is able to facilitate the resale of the package to a second party who also wishes to be able to waltz in an exoskeleton. Importantly, the distributor is able to facilitate a safe transfer of this package through the validation step, which in some cases takes into account variable exoskeleton user attributes. If the distributor determines that the second party cannot safely use a particular exoskeleton trajectory sequence package, the distributor can block the transfer. Otherwise, the transaction proceeds as described above. Alternatively, the distributor may determine that the second party cannot safely use the package but that the second party can contract with an exoskeleton trajectory editor or tuner. This editor or tuner can then make the package safe to use for the second party, as will be discussed in more detail below in connection with a third embodiment of the present invention.

Figure 4A:
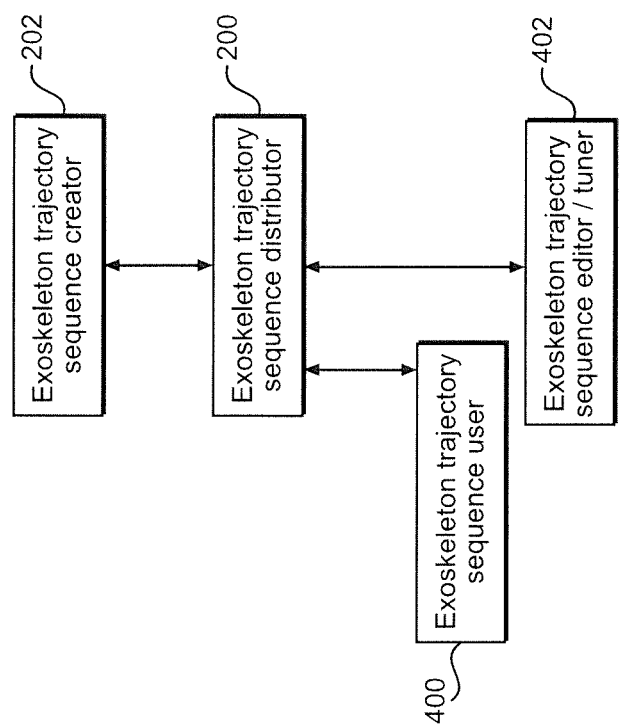
FIG. 4A is a block diagram showing the parties that are communicating in a third embodiment of the present invention.
Figure 4B:
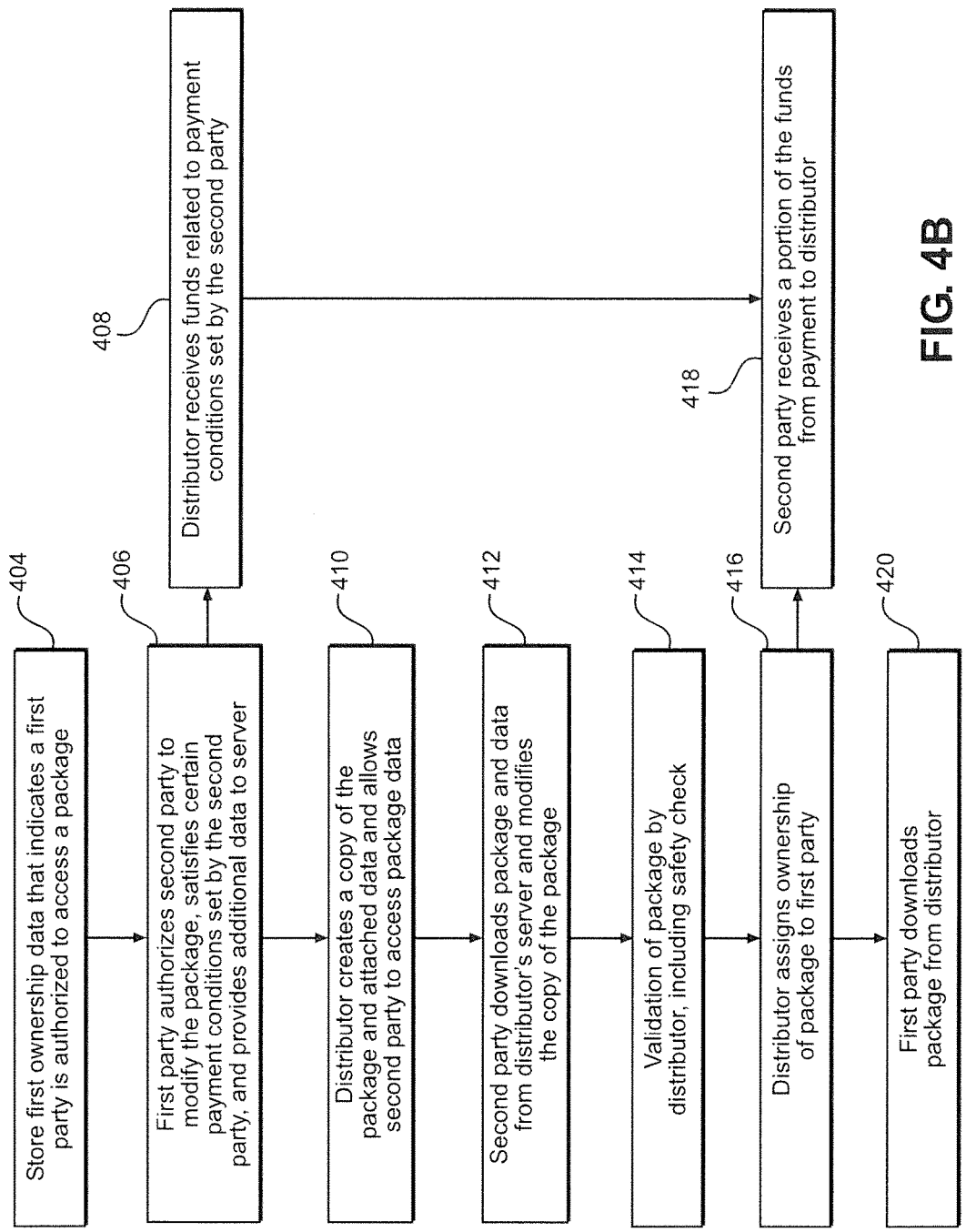
FIG. 4B is a flowchart in accordance with the third embodiment in which an owner of an exoskeleton trajectory sequence can hire a second party to modify a copy of said exoskeleton trajectory sequence using a system similar to the first embodiment, with distributor validation of the exoskeleton trajectory sequence for parameters including safety prior to transfer of the modified trajectory sequence.

With reference to FIG. 4A, distributor 200 is shown in communication with creator 202, an exoskeleton trajectory sequence user 400 and an exoskeleton trajectory sequence editor (or tuner) 402 in accordance with a third embodiment of the present invention. A flow diagram in accordance with the third embodiment is illustrated in FIG. 4B. With continued reference to FIG. 4B, at step 404, distributor 200 stores first ownership data, which indicates that user 400 is authorized to access an exoskeleton trajectory sequence package (this package having been acquired by user 400 in accordance with the first embodiment). At step 406, user 400 indicates to distributor 200 that user 400 authorizes editor 402 to modify the package. User 400 also satisfies certain payment conditions set by editor 402 and provides additional data to a distribution server. The data is attached to the trajectories package and can include physical attributes of user 400 and/or information on the changes desired to the package by user 400. At step 408, distributor 200 receives funds related to the payment conditions set by editor 402. At step 410, distributor 200 creates a copy of the package and attached data and allows editor 402 to access the package and data. At step 412, editor 402 downloads the copy of the package and data from the server of distributor 200 and then modifies the package to better suit the needs of the user 400 in accordance with the additional data provided by the first party in step 406. At step 414, a validation of the modified package is performed by distributor 200 including a safety check, which, in some cases, takes into account the attributes and/or requirements of user 400 provided by user 400 in step 406. Upon validation of the modified package in step 414, distributor 200 assigns ownership of the modified package to user 400 in step 416, at which point editor 402 receives a portion of the funds from payment to distributor in step 418. User 400 then downloads the modified package from distributor in step 420.

Figure 4C:
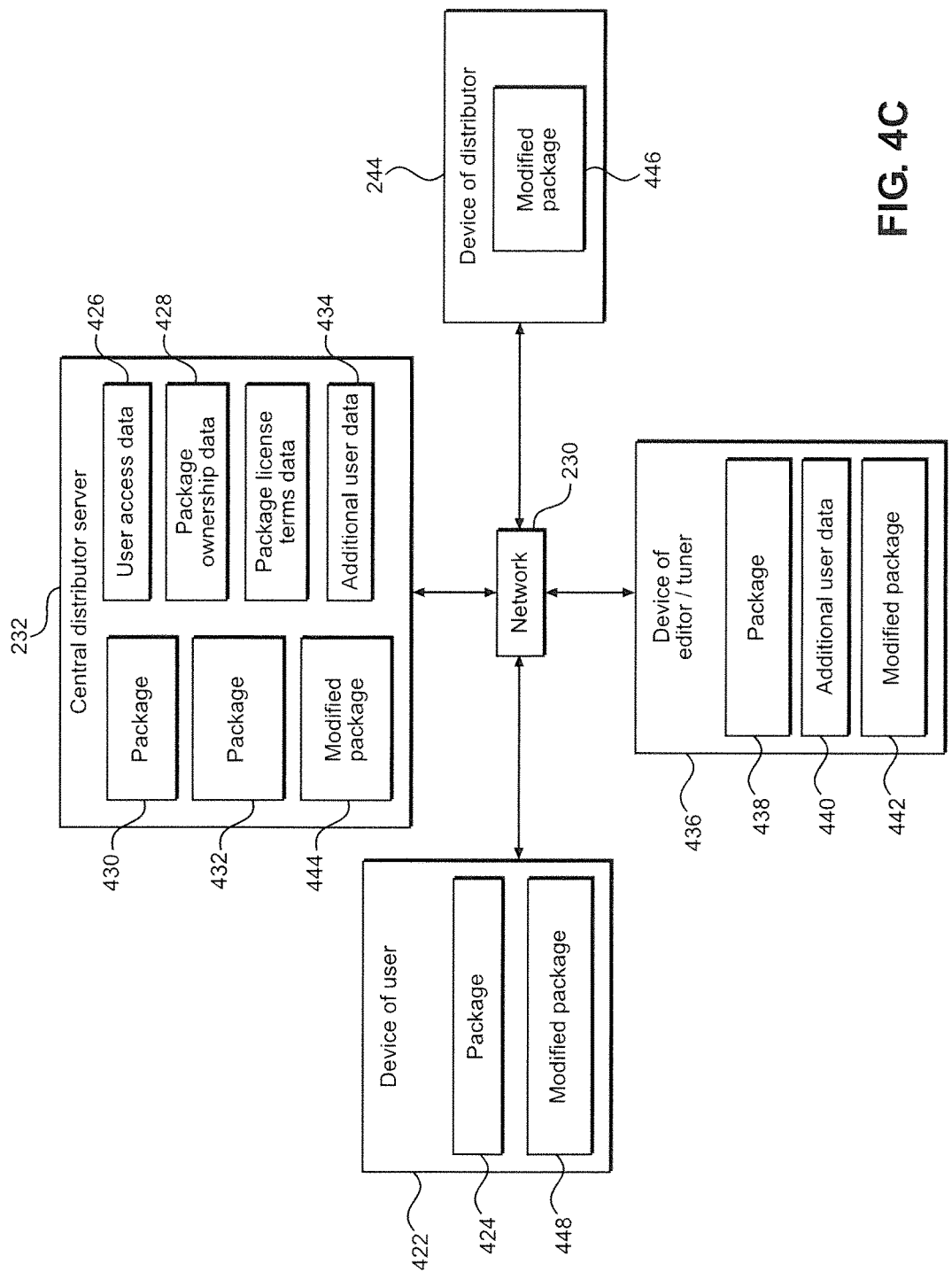
FIG. 4C is a block diagram showing the devices and digital content in communication in the third embodiment.

With reference to FIG. 4C, a block diagram shows the devices and digital content in communication in accordance with the third embodiment. A device 422 of user 400 contains a stored digital content item: an exoskeleton trajectory sequence package 424. Device 422 is in communication with network 230, which is also in communication with server 232. Server 232 knows the identity of device 422 based on user access data 426. In addition, package ownership data 428 is stored within server 232. Based on user access data 426 and ownership data 428, server 232 confirms that device 422 is an authorized licensee, or other owner type, of trajectories package 424, which is a duplicate of an exoskeleton trajectory sequence package 430 that is stored on server 232. Device 422 indicates to server 232, via network 230, that it wishes to have package 424 edited by either: 1) a specific person or entity that is an exoskeleton trajectory sequence package editor or tuner; or 2) by any available "licensed" editor or tuner. Server 232 generates an exoskeleton trajectory sequence package 432, which is a duplicate of package 430, and prompts device 422 to provide additional data. Device 422 then uploads this additional data to server 232 where it is stored as additional user data 434 and attached to package 430. A device 436 of editor 402 then downloads both package 432 and additional user data 434, storing them as an exoskeleton trajectory sequence package 438 and additional user data 440. When editor 402 has finished modifying package 438 based on additional user data 440, this modified file is stored as modified exoskeleton trajectory sequence package 442, which is then uploaded to server 232 and saved as a modified exoskeleton trajectory sequence package 444. Modified package 444 is then downloaded by device 244 of distributor 200 where it is saved as a modified exoskeleton trajectory sequence package 446. Upon successful validation of modified package 446 by device 244, device 244 signals server 232 to alter user access data 426 and package ownership data 428 so as to allow device 422 of user 400 to access modified package 444. At this point, device 422 downloads modified package 444 and saves this content as a modified trajectory sequence package 448.

As an example of the third embodiment, consider the case of a disabled exoskeleton wearer who has a daughter who is to be married in the future. This wearer wants to be able to dance with his daughter at her upcoming wedding and, prior to the wedding, purchases an exoskeleton trajectory sequence package that allows the wearer to dance the waltz. This waltz package was written for a person approximately 5'10" and 150 lbs. However, the disabled exoskeleton wearer is 6'7" and 240 lbs. It is possible that the package might provide some function, but, for graceful dance movements, an optimization of the package is required. Accordingly, the wearer contacts, though a distributor, an expert in tuning packages for dance movements. This expert then edits a copy of the package licensed by the wearer and uploads a modified package to the distributor's server. The wearer then transfers the modified package to his exoskeleton, which allows the wearer to dance gracefully at his daughter's wedding.

In some embodiments, the distributor is the exoskeleton manufacturer, while, in other embodiments, the distributor is a subsidiary of the exoskeleton manufacturer. The distributor can also be an entity partnered with the exoskeleton manufacturer, a contractor of the exoskeleton manufacturer, or a licensee of the exoskeleton manufacturer. Additionally, in some embodiments, the exoskeleton user or wearer is a disabled person who is receiving treatment from a physical therapist. In other embodiments, the exoskeleton user is a disabled person who is operating the exoskeleton, an abled-bodied person, or an able-bodied person working with a trainer. In some embodiments, the exoskeleton trajectory sequence creator is a physical therapist who creates exoskeleton trajectories, in whole or in part, while working with one or more disabled patients, wearing exoskeletons, over one or more sessions of treatment. In other embodiments, the exoskeleton trajectory sequence creator is a physical therapist who creates exoskeleton trajectories while working with one or more able-bodied persons, wearing exoskeletons, over one or more sessions. In other embodiments, the creator is a physical therapist who creates exoskeleton trajectories while wearing an exoskeleton. In still other embodiments, the creator is a physical therapist who creates exoskeleton trajectories without the use of an exoskeleton, including but not limited to use of motion capture techniques or in silico modeling and composition of trajectories (i.e., on computer or via computer simulation). In addition, a person who is not a physical therapist but who is skilled in the art of exoskeleton trajectory sequence design can fill the role of creator. In some embodiments, the creator is skilled in the specific activities related to the exoskeleton trajectory sequence being created, such a dancing or another athletic activity. Also, in some embodiments, the editor or tuner is the exoskeleton manufacturer. In other embodiments, the editor or tuner is a subsidiary of the exoskeleton manufacturer, an entity partnered with the exoskeleton manufacturer, a contractor of the exoskeleton manufacturer, or a licensee of the exoskeleton manufacturer.

In some embodiments, the devices (of the creator, distributor, user or editor) are computers, and, in other embodiments, the devices are exoskeletons and linked control systems. Alternatively, a computer in combination with an exoskeleton and linked control system can constitute one of the devices. In any case, it should be recognized that the devices need not all be of the same type in a given embodiment. The package license terms can take any of a number of forms including the purchase of a copy of an exoskeleton trajectory sequence package with permanent usage rights, a lease or term subscription to a package, or even an outright purchase of all ownership rights to all copies of a package. Also, payments can be facilitated through third-party payment service vendors. In some embodiments, the network is wireless, while, in other embodiments, the network is wired. Additionally, in some embodiments, an exoskeleton trajectory sequence package includes additional features that potentiate use of the exoskeleton trajectory sequence by the exoskeleton wearer, including interfaces related to activation of the trajectory sequence, guidance of the exoskeleton during the trajectory sequence, or exoskeleton wearer feedback related to the trajectory sequence. In some embodiments, the creator and distributor of the package receive monitoring data on the use and performance of the package Based on the above, it should be readily apparent that the present invention provides a device and method that allows exoskeleton trajectory sequence creators to distribute exoskeleton trajectory sequences to exoskeleton users. In addition, the present invention provides a device and method that ensures that the trajectory sequences are safe. Although described with reference to preferred embodiments, it should be readily understood that various changes or modifications could be made to the invention without departing from the spirit thereof. In general, the invention is only intended to be limited by the scope of the following claims.

The invention claimed is:

1. A method for transferring an exoskeleton trajectory sequence using at least one server remote from a first device including a controller, the method comprising:
transferring, with the at least one server, the exoskeleton trajectory sequence to the first device where the exoskeleton trajectory sequence is validated, wherein validating the exoskeleton trajectory sequence includes performing a safety check in which a determination is made with the controller as to whether the exoskeleton trajectory sequence is safe for use with exoskeletons, the first device includes a first exoskeleton, the safety check includes performing a physical test of the exoskeleton trajectory sequence using the first exoskeleton, performing the physical test includes causing the first exoskeleton to move and receiving data from a sensor of the first exoskeleton, and causing the first exoskeleton to move includes causing the first exoskeleton to perform the exoskeleton trajectory sequence; and
receiving, from the first device, the exoskeleton trajectory sequence or confirmation that the exoskeleton trajectory sequence is valid with the at least one server, wherein the exoskeleton trajectory sequence includes prescribed positions of joints of an exoskeleton over time or a force profile of actuators of the exoskeleton.

2. The method of claim 1, wherein the physical test is performed while the first exoskeleton is worn by a person or an anthropomorphic device.

3. The method of claim 1, further comprising:
receiving the exoskeleton trajectory sequence from a creator of the exoskeleton trajectory sequence with the at least one server prior to transferring the exoskeleton trajectory sequence to the first device, the exoskeleton trajectory sequence having been created using a first second exoskeleton of the creator.

4. The method of claim 1, further comprising:
receiving, from a first exoskeleton user, a request for the exoskeleton trajectory sequence to be transferred with the at least one server prior to transferring the exoskeleton trajectory sequence to the first device;
transferring the exoskeleton trajectory sequence to a second exoskeleton user after the exoskeleton trajectory sequence is validated; and
preventing the first exoskeleton user from using or accessing the exoskeleton trajectory sequence.

5. The method of claim 4, wherein the validation includes determining whether the exoskeleton trajectory sequence is safe for use by the second exoskeleton user.

6. The method of claim 5, wherein determining whether the exoskeleton trajectory sequence is safe for use by the second exoskeleton user includes taking into account physical attributes of the second exoskeleton user.

7. The method of claim 4, wherein transferring the exoskeleton trajectory sequence to the second exoskeleton user includes transferring the exoskeleton trajectory sequence to a second exoskeleton of the second exoskeleton user.

8. The method of claim 1, further comprising:
receiving, from an exoskeleton user, a request for the exoskeleton trajectory sequence to be edited with the at least one server prior to transferring the exoskeleton trajectory sequence to the first device;
transferring the exoskeleton trajectory sequence to a second device, where the exoskeleton trajectory sequence is edited, prior to transferring the exoskeleton trajectory sequence to the first device; and
transferring the exoskeleton trajectory sequence to the exoskeleton user after the exoskeleton trajectory sequence is validated.

9. The method of claim 8, wherein the validation includes determining whether the exoskeleton trajectory sequence is safe for use by the exoskeleton user.

10. The method of claim 9, wherein determining whether the exoskeleton trajectory sequence is safe for use by the exoskeleton user includes taking into account physical attributes of the exoskeleton user.

11. The method of claim 8, wherein transferring the exoskeleton trajectory sequence to the exoskeleton user includes transferring the exoskeleton trajectory sequence to a second exoskeleton of the exoskeleton user.

12. The method of claim 8, wherein the second device includes a second exoskeleton, and transferring the exoskeleton trajectory sequence to the second device includes transferring the exoskeleton trajectory sequence to the second exoskeleton.

13. A system for transferring an exoskeleton trajectory sequence comprising:
- a first device including a controller, wherein the first device is configured to validate the exoskeleton trajectory sequence, validating the exoskeleton trajectory sequence includes performing a safety check in which a determination is made with the controller as to whether the exoskeleton trajectory sequence is safe for use with exoskeletons, the first device includes a first exoskeleton, the safety check includes performing a physical test of the exoskeleton trajectory sequence using the first exoskeleton, performing the physical test includes causing the first exoskeleton to move and receiving data from a sensor of the first exoskeleton, and causing the first exoskeleton to move includes causing the first exoskeleton to perform the exoskeleton trajectory sequence; and
- at least one server remote from the first device, wherein the at least one server is configured to transfer the exoskeleton trajectory sequence to the first device and receive, from the first device, the exoskeleton trajectory sequence or confirmation that the exoskeleton trajectory sequence is valid, and the exoskeleton trajectory sequence includes prescribed positions of joints of an exoskeleton over time or a force profile of actuators of the exoskeleton.

14. The system of claim 13, wherein the at least one server is configured to:
- receive, from a first exoskeleton user, a request for the exoskeleton trajectory sequence to be transferred prior to transferring the exoskeleton trajectory sequence to the first device; and
- transfer the exoskeleton trajectory sequence to a second exoskeleton user after the exoskeleton trajectory sequence is validated.

15. The system of claim 13, wherein the at least one server is configured to:
- receive, from an exoskeleton user, a request for the exoskeleton trajectory sequence to be edited prior to transferring the exoskeleton trajectory sequence to the first device;
- transfer the exoskeleton trajectory sequence to a second device, where the exoskeleton trajectory sequence is edited, prior to transferring the exoskeleton trajectory sequence to the first device; and
- transfer the exoskeleton trajectory sequence to the exoskeleton user after the exoskeleton trajectory sequence is validated.

* * * * *